United States Patent
Matsue

(10) Patent No.: US 7,582,599 B1
(45) Date of Patent: Sep. 1, 2009

(54) DETERGENT COMPOSITION COMPRISING A MIXTURE OF TWO ANIONIC, A NONIONIC, AND AN AMPHOTERIC SURFACTANT

(75) Inventor: Yukako Matsue, Kanagawa (JP)

(73) Assignee: Kracie Home Products, Ltd., Tokyo (JP)

( * ) Notice: Subject to any disclaimer, the term of this patent is extended or adjusted under 35 U.S.C. 154(b) by 0 days.

(21) Appl. No.: 12/256,805

(22) Filed: Oct. 23, 2008

(51) Int. Cl.
*C11D 1/94* (2006.01)
*C11D 3/37* (2006.01)
*C11D 3/04* (2006.01)

(52) U.S. Cl. .................. 510/427; 510/119; 510/123; 510/125; 510/127; 510/130; 510/135; 510/136; 510/155; 510/156; 510/421; 510/422; 510/426; 510/490

(58) Field of Classification Search .......... 510/119, 510/123, 125, 127, 130, 135, 136, 155, 156, 510/421, 422, 426, 427, 490
See application file for complete search history.

(56) References Cited

U.S. PATENT DOCUMENTS

| 2004/0092414 A1* | 5/2004 | Clapp et al. ............. 510/130 |
| 2004/0220063 A1* | 11/2004 | Chappell et al. ........ 510/130 |
| 2008/0057021 A1* | 3/2008 | Dykstra et al. ......... 424/78.02 |
| 2008/0139432 A1* | 6/2008 | Peffly et al. ............ 510/122 |

FOREIGN PATENT DOCUMENTS

| GB | 2192194 A | 1/1988 |
| JP | 4273811 A | 9/1992 |
| JP | 10245323 A | 9/1998 |
| JP | 2000319140 A | 11/2000 |

* cited by examiner

*Primary Examiner*—Charles I Boyer
(74) *Attorney, Agent, or Firm*—The Webb Law Firm

(57) ABSTRACT

An object is to provide a detergent composition which is excellent in conditioning effects, and having sufficient foaming property and having suitable viscosity. It can be accomplished by a detergent composition comprising (A) triethanolamine salt of N-acylsarcosine, (B) triethanolamine polyoxyethylene lauryl ether sulfate, (C) polyoxypropylene fatty acid isopropanolamide, (D) a cationic polymer, (E) a water-soluble inorganic salt and (F) an amphoteric surfactant.

20 Claims, No Drawings

DETERGENT COMPOSITION COMPRISING A MIXTURE OF TWO ANIONIC, A NONIONIC, AND AN AMPHOTERIC SURFACTANT

TECHNICAL FIELD

The present invention relates to a detergent composition excellent in conditioning effects, and having a sufficient foaming property and having suitable viscosity.

BACKGROUND ART

For a detergent, a washing power and good foaming characteristics have been required. At the same time, in recent years, due to heightening of care consciousness of consumers, in addition to the basic characteristics as a detergent, a feeling of use during washing and a good feeling of finishing after washing, and conditioning effects have been tend to be required.

As a conditioning agent for a detergent, a cationic polymer, a polymer silicone, a protein, an amino acid, etc., have been formulated (for example, see Patent Literatures 1 to 3.). However, they are not yet sufficient in the points of a feeling of use during washing and a good feeling of finishing. Also, as a detergent having highly foaming property, an anionic surfactant such as α-olefin sulfonate, sodium lauryl sulfate, sodium polyoxyethylene lauryl ether sulfate, etc., has been used, but these detergents are weak in conditioning effects a preferred feeling of use during washing could not be obtained. As a low-stimulus detergent, an amino acid type surfactant such as an acylsarcosine salt, an acylmethyl-β-alanine salt, acylglutamate, etc., has been used (for example, see Patent Literatures 1 and 4), but these detergents are formulated into a detergent with a high concentration, a suitable viscosity cannot easily be obtained, and even if a suitable viscosity is temporarily obtained, it decreases with a lapse of time so that preferred feeling of use cannot be obtained.

[Patent Literature 1] JP 3064037B
[Patent Literature 2] JP 63-45213A
[Patent Literature 3] JP 2000-319140A
[Patent Literature 4] JP 3644566B

DISCLOSURE OF THE INVENTION

Problems to be Solved by the Invention

In the above-mentioned circumstances, it has been desired to develop a technique which resolves the above-mentioned defects. That is, an object of the present invention is to provide a detergent composition excellent in conditioning effects, and having a sufficient foaming property and having suitable viscosity.

Means to Solve the Problems

The present inventor has earnestly studied in view of the above-mentioned circumstances and as a result, she has found out that a detergent composition containing a specific surfactant, a cationic polymer and an inorganic salt can accomplish the above-mentioned objects whereby the present invention has been completed. That is, the present invention relates to a detergent composition comprising (A) triethanolamine salt of N-acylsarcosine, (B) triethanolamine polyoxyethylene lauryl ether sulfate, (C) a polyoxypropylene fatty acid isopropanolamide, (D) a cationic polymer, (E) a water-soluble inorganic salt, and (F) an amphoteric surfactant.

Effects of the Invention

According to the present invention, it can be provided a detergent composition excellent in conditioning effects, having a sufficient foaming property, and having suitable viscosity.

BEST MODE TO CARRY OUT THE INVENTION

As (A) the triethanolamine salt of N-acylsarcosine to be used in the present invention, there may be mentioned, for example, triethanolamine lauroyl sarcosinate, triethanolamine myristoyl sarcosinate, etc. A formulation amount of the triethanolamine salt of N-acylsarcosine is preferably 1.0% to 30.0% by weight (hereinafter merely referred to as "%".), more preferably 5.0 to 20.0% based on the whole composition. This is because, if a formulation amount of the triethanolamine salt of N-acylsarcosine is increased, conditioning effects (for example, a feeling of use during washing and a good feeling of finishing after washing, etc.) are heightened but viscosity is lowered. Thus, to obtain sufficient conditioning effects, 1.0% or more is preferred, and for maintaining suitable viscosity and to obtain a sufficient foaming property, 30.0% or lower is preferred.

A formulation amount of the (B) triethanolamine polyoxyethylene lauryl ether sulfate to be used in the present invention is not specifically limited, and it is preferably 0.1 to 5.0%, more preferably 0.5 to 3.0% based on the whole composition. This is because, if a formulation amount of the triethanolamine polyoxyethylene lauryl ether sulfate is increased, viscosity is heightened, but conditioning effects are tend to be inhibited, so that it is preferably 0.1% or more for maintaining suitable viscosity, and for obtaining sufficient conditioning effects, 5.0% or lower is preferred.

As (C) the polyoxypropylene fatty acid isopropanolamide to be used in the present invention, there may be mentioned, for example, polyoxypropylene lauric acid isopropanolamide, polyoxypropylene myristic acid isopropanolamide, polyoxypropylene stearic acid isopropanolamide, polyoxypropylene palm oil fatty acid isopropanolamide, polyoxypropylene palm kernel oil fatty acid isopropanolamide, etc. A formulation amount thereof is not particularly limited, and it is preferably 0.5 to 15.0%, more preferably 1.0 to 5.0% based on the whole composition. This is because, if a formulation amount of the polyoxypropylene fatty acid isopropanolamide is increased, viscosity is heightened, but foaming property is tend to be inhibited, so that it is preferably 0.5% or more to maintain suitable viscosity and to obtain a sufficient foaming property, and to make the viscosity not to inhibit the foaming property, it is preferably 15.0% or lower.

(D) the cationic polymer to be used in the present invention is not specifically limited, and there may be mentioned, for example, cationic cellulose derivative, cationic starch, cationic guar gum derivative, diallyl quaternary ammonium salt polymerized product, diallyl quaternary ammonium salt/acrylamide copolymerized product, quaternary polyvinylpyrrolidone derivative, etc. These cationic polymers are optionally selected, and 1 or 2 or more kinds thereof may be used. A formulation amount of these cationic polymers is not specifically limited, and it is preferably 0.1 to 3.0%, more preferably 0.3 to 1.5% based on the whole composition. This is because, if a formulation amount of the cationic polymer is increased, conditioning effects are heightened, but it is too much, it tends to be precipitated in the detergent so that to obtain sufficient conditioning effects, it is preferably 0.1% or more, and to be solubilized the same without precipitating in the detergent, 3.0% or lower is preferred.

(E) the water-soluble inorganic salt to be used in the present invention is at least one of salts formed by a monovalent cation comprising a sodium ion, a potassium ion and an ammonium ion and/or a divalent cation comprising a magnesium ion and a calcium ion, with an anion comprising a chlorine ion, a sulfate ion, a phosphate ion, a carbonate ion and a nitrate ion. Suitable examples are mentioned, for example, sodium chloride, sodium carbonate, sodium sulfate, sodium hydrogen sulfate, sodium phosphate, sodium hydrogen phosphate, potassium chloride, potassium sulfate, potassium hydrogen sulfate, potassium phosphate, potassium hydrogen phosphate, potassium dihydrogen phosphate, magnesium chloride, calcium chloride, ammonium sulfate, ammonium phosphate, magnesium sulfate, etc., and sodium chloride, magnesium chloride, calcium chloride and magnesium sulfate are more preferred. A formulation amount of these water-soluble inorganic salts is not particularly limited, and it is preferably 0.1 to 3.0%, more preferably 0.3 to 1.5% based on the whole composition. This is because, if a formulation amount of the water-soluble inorganic salt is increased, viscosity is heightened, but it is too much, viscosity is lowered so that to make the detergent suitable viscosity, 0.1% to 3.0 is preferred.

(F) the amphoteric surfactant to be used in the present invention is not specifically limited, and there may be mentioned, for example, lauryl betaine, lauroylamide propylbetaine, 2-alkyl-N-carboxymethyl-N-hydroxyethyl-imidazolinium betaine, etc. These amphoteric surfactants are optionally selected, and 1 or 2 or more kinds thereof may be used. A formulation amount of these amphoteric surfactants is not specifically limited, and it is preferably 1.0 to 10.0%, more preferably 3.0 to 8.0% based on the whole composition. This is because, if a formulation amount of the amphoteric surfactant is increased, conditioning effects are heightened and viscosity is also heightened, but the viscosity becomes too high, it causes a tendency of inhibiting conditioning effects or a foaming property. Thus, for obtaining sufficient conditioning effects, it is preferably 1.0% or more, and to maintain suitable viscosity, 10.0% or lower is preferred.

In the detergent composition of the present invention, in addition to the above-mentioned components, a component(s) usually employed for the detergent composition depending on the purposes can be optionally formulated within the range which can accomplish the objects of the present invention. As such a component, there may be mentioned, for example, a nonionic surfactant, a cationic surfactant, a humectant, a silicone derivative, an oil, a vegetable extract, a viscosity modifier, a pearly sheen agent, a chemical, a preservative, a chelator, an anti-oxidant, a pH controller, a dye, a perfume, etc.

The detergent composition of the present invention is not particularly limited by the objects and preparation forms, and it can be used for hair shampoo, body shampoo, hand soap, face washer, etc. These can be prepared by formulating the detergent composition of the present invention according to the conventional manner.

EXAMPLE

The present invention is explained in detail by referring to Examples, but the present invention is not limited by these.

Before stating Examples, test methods and evaluation methods employed in each Example are explained.

Test Method of Feeling of Use During Washing Hair (Conditioning Effects)

Ten panelists were washed ones hair with a sample (in the following, it is merely referred to as "sample") of the respective Examples, with regard to the feeling of use such as wet comb ability during washing the hair, presence or absence of creak of hair, etc., these matters were judged with three levels of "good", "normal" and "poor", and evaluated with a number of persons who answered the judgment results as "good".

The judgment criteria is as follows.

| | |
|---|---|
| ⊚: Extremely excellent | A number of tested persons who answered as "good" is 8 persons or more |
| ○: Excellent | A number of tested persons who answered as "good" is 6 persons or more and less than 8 persons |
| Δ: Poor | A number of tested persons who answered as "good" is 4 persons or more and less than 6 persons |
| X: Markedly poor | A number of tested persons who answered as "good" is less than 4 persons |

Test Method of Finished Feeling of Hair After Drying Hair (Conditioning Effects)

Ten panelists were washed ones hair with a sample, with regard to a moisture, softness and flexibility of hair after drying the washed hair, etc., these matters were judged with three levels of "good", "normal" and "poor", and evaluated with a number of persons who answered the judgment results as "good".

The judgement criteria is as follows.

| | |
|---|---|
| ⊚: Extremely excellent | A number of tested persons who answered as "good" is 8 persons or more |
| ○: Excellent | A number of tested persons who answered as "good" is 6 persons or more and less than 8 persons |
| Δ: Poor | A number of tested persons who answered as "good" is 4 persons or more and less than 6 persons |
| X: Markedly poor | A number of tested persons who answered as "good" is less than 4 persons |

Test Method of Foaming Property

An aqueous solution (using artificial hard water containing 50 ppm of $CaCO_3$, 40° C.) of each sample was prepared so that an activator concentration of 2%, and the test was carried out according to the Ross-Miles test method.

The judgement criteria is as follows.

| | | |
|---|---|---|
| ⊚: Excellent foaming | Foam height | 250 mm or more |
| ○: Good foaming | Foam height | 210 mm or more and less than 250 mm |
| Δ: Usual forming | Foam height | 170 mm or more and less than 210 mm |
| X: Poor foaming | Foam height | less than 170 mm |

Viscosity Measurement Method

Measurement device: By using a Brookfield viscometer (No. 3, 12 rotations, 30 seconds), a viscosity was measured at a measurement temperature of 20° C.

The judgement criteria is as follows.

| ⊚: Optimum viscosity | 2000 to 6000 mPa·s |
|---|---|
| ○: Suitable viscosity | 1000 to 2000 mPa·s |
| Δ: Viscosity is too high | 6000 mPa·s or more |
| X: Viscosity is too low | less than 1000 mPa·s |

Examples 1 to 4 and Comparative Examples 1 to 9
(Hair Shampoo)

Shampoos having the formulation compositions shown in Table 1 were prepared according to the conventional manner, and their feeling of use during washing hair, finished feeling of hair after drying hair, a foaming property and a viscosity were examined. The results are shown in Table 1.

As can be clearly seen from Table 1, the detergent compositions according to the present invention are found to be excellent characteristics as compared with the compositions of Comparative examples.

Example 5 Shampoo

| | |
|---|---|
| Triethanolamine lauroyl sarcosinate | 12.0 |
| Triethanolamine polyoxyethylene lauryl ether sulfate | 4.0 |
| Polyoxypropylene palm oil fatty acid monoethanolamide | 3.5 |
| Palm oil fatty acid monoethanolamide | 1.0 |
| Palm oil fatty acid amide propylbetaine | 6.0 |
| Cationic cellulose derivative (trade name: CATINAL HC-200 [available from TOHO Chemical Industry Co., Ltd.]) | 0.3 |
| O-[2-hydroxy-3-(trimethylammonio) propyl]-guar gum chloride | 0.1 |
| Polyoxypropylene palm oil fatty acid Isopropanolamide | 3.0 |
| Ethylene glycol distearate | 2.0 |
| Soapberry extract (trade name: Mukurossi extract [available from MARUZEN PHARMACEUTICALS CO., LTD.]) | 0.5 |

TABLE 1

| | Example | | | | Comparative example | | | | | | | | |
|---|---|---|---|---|---|---|---|---|---|---|---|---|---|
| | 1 | 2 | 3 | 4 | 1 | 2 | 3 | 4 | 5 | 6 | 7 | 8 | 9 |
| Triethanolamine lauroyl sarcosinate | 10 | 2 | 18 | 10 | — | 10 | — | — | 10 | 10 | 10 | 10 | 10 |
| Sodium lauroyl sarcosinate | — | — | — | — | 10 | — | — | — | — | — | — | — | — |
| Monotriethanolamine N-cocoyl-L-glutamate | — | — | — | — | — | — | 10 | — | — | — | — | — | — |
| Triethanolamine polyoxyethylene lauryl ether sulfate | 1 | 5 | 0.5 | 1 | 1 | — | 1 | 10 | — | 1 | 1 | 1 | 1 |
| Sodium polyoxyethylene lauryl ether sulfate | — | — | — | — | — | 1 | — | — | — | — | — | — | — |
| Polyoxypropylene palm oil fatty acid isopropanolamide | 4 | 5 | 4 | 14 | 4 | 4 | 4 | 4 | 4 | — | 4 | 4 | 4 |
| Palm oil fatty acid diethanolamide | — | — | — | — | — | — | — | — | — | 4 | — | — | — |
| Cationic cellulose derivative (trade name: Leoguard MGP [available from Lion Corporation]) | 0.3 | 0.3 | 0.3 | 0.2 | 0.3 | 0.3 | 0.3 | 0.3 | 0.3 | 0.3 | — | — | 0.3 |
| Cationic guar gum derivative (trade name: Jaguar C-17 [available from Rhodia Inc.]) | 0.1 | 0.2 | 0.2 | — | 0.1 | 0.1 | 0.1 | 0.1 | 0.1 | 0.1 | — | 0.3 | 0.2 |
| Dimethyldiallyl ammonium chloride-acrylamide copolymer solution (trade name: Lipoflow MN [available from Lion Corporation]) | 0.5 | — | — | 0.2 | 0.5 | 0.5 | 0.5 | 0.5 | 0.5 | 0.5 | — | — | — |
| Sodium chloride | 0.6 | — | 0.6 | 0.2 | 0.6 | 0.6 | 0.6 | 0.6 | 0.6 | 0.6 | 0.6 | — | 0.6 |
| Magnesium chloride | — | 0.2 | — | — | — | — | — | — | — | — | — | — | — |
| Palm kernel oil fatty acid amide propylbetaine | 6 | 5 | 5 | 5 | 6 | 6 | 6 | 6 | 6 | 6 | 6 | 6 | — |
| 2-Alkyl-N-carboxymethyl-N-hydroxy-ethylimidazolinium betaine | — | 2 | 2 | — | — | — | — | — | — | — | — | — | — |
| Purified water | Reminder | Reminder | Reminder | Reminder | Reminder | Reminder | Reminder | Reminder | Reminder | Reminder | Reminder | Reminder | Reminder |
| Evaluation results | — | — | — | — | — | — | — | — | — | — | — | — | — |
| Feeling of use during washing hair | ⊚ | ○ | ⊚ | ⊚ | X | X | ○ | X | ⊚ | ⊚ | X | ⊚ | Δ |
| Finished feeling after drying washed hair | ⊚ | ○ | ⊚ | ⊚ | Δ | ○ | ○ | X | ⊚ | ⊚ | Δ | ⊚ | Δ |
| Foaming property | ⊚ | ⊚ | ⊚ | Δ | ⊚ | ⊚ | Δ | ⊚ | ○ | ⊚ | ○ | ⊚ | ○ |
| Viscosity | ⊚ | ⊚ | ○ | Δ | ⊚ | ⊚ | ○ | ⊚ | ○ | ⊚ | ○ | X | X |
| Viscosity of preserved product for 6 months at room temperature | ⊚ | ⊚ | ○ | ⊚ | ⊚ | ⊚ | X | ⊚ | X | X | ○ | X | X |

-continued

| | |
|---|---|
| Blackberry lily extract | 0.1 |
| (trade name: Hiougi liquid [available from Ichimaru Pharcos Co., Ltd.]) | |
| Camellia extract | 0.1 |
| (trade name: Camellia seed extract [available from MARUZEN PHARMACEUTICALS CO., LTD.]) | |
| Citric acid | 0.3 |
| Sodium benzoate | 0.5 |
| EDTA | 0.1 |
| Sodium chloride | 0.5 |
| Caramel | 0.2 |
| Perfume | 0.5 |
| Purified water | balance |

A shampoo having the above-mentioned composition was prepared according to the conventional manner, and when feeling of use during washing hair, finished feeling of hair after drying hair, a foaming property and a viscosity were evaluated, either of the characteristics was excellent to obtain good results.

Example 6 Body Shampoo

| | |
|---|---|
| Potassium laurate | 5.0 |
| Potassium myristate | 4.0 |
| Potassium palmitate | 4.0 |
| Triethanolamine myristoyl sarcosinate | 5.0 |
| Triethanolamine polyoxyethylene lauryl ether sulfate | 1.0 |
| Polyoxypropylene palm oil fatty acid monoethanolamide | 4.0 |
| O-[2-hydroxy-3-(trimethylammonio) propyl]-guar gum chloride | 0.3 |
| 2-Alkyl-N-carboxymethyl-N-hydroxy-ethylimidazolinium betaine | 2.0 |
| Palm oil fatty acid amide propylbetaine | 2.0 |
| Ethylene glycol distearate | 2.0 |
| Hydroxypropyl methyl cellulose | 0.3 |
| Conc. glycerin | 1.0 |
| Propyleneglycol | 5.0 |
| Palm oil fatty acid monoethanolamide | 1.0 |
| Peach leaf extract | 1.0 |
| EDTA | 0.1 |
| Perfume | 0.5 |
| Purified water | balance |

A body shampoo having the above-mentioned composition was prepared according to the conventional manner, and when the feeling of use and a foaming property were evaluated, either of the characteristics was excellent to obtain good results.

UTILIZABILITY IN INDUSTRY

According to the present invention, a detergent composition excellent in conditioning effects, and having a sufficient foaming property and having suitable viscosity can be provided.

The invention claimed is:
1. A detergent composition which comprises
(A) triethanolamine salt of N-acylsarcosine,
(B) triethanolamine polyoxyethylene lauryl ether sulfate,
(C) polyoxypropylene fatty acid isopropanolamide,
(D) a cationic polymer,
(E) a water-soluble inorganic salt, and
(F) an amphoteric surfactant.

2. The detergent composition according to claim 1, wherein (A) the triethanolamine salt of N-acylsarcosine is at least one selected from the group consisting of triethanolamine lauroyl sarcosinate and triethanolamine myristoyl sarcosinate.

3. The detergent composition according to claim 1, wherein a formulation amount of (A) the triethanolamine salt of N-acylsarcosine is 1.0% to 30.0% by weight based on the whole composition.

4. The detergent composition according to claim 1, wherein a formulation amount of (A) the triethanolamine salt of N-acylsarcosine is 5.0 to 20.0% by weight based on the total weight of the composition.

5. The detergent composition according to claim 1, wherein a formulation amount of (B) the triethanolamine polyoxyethylene lauryl ether sulfate is 0.1 to 5.0% by weight based on the total weight of the composition.

6. The detergent composition according to claim 1, wherein a formulation amount of (B) the triethanolamine polyoxyethylene lauryl ether sulfate is 0.5 to 3.0% by weight based on the total weight of the composition.

7. The detergent composition according to claim 1, wherein (C) the polyoxypropylene fatty acid isopropanolamide is at least one selected from the group consisting of polyoxypropylene lauric acid isopropanolamide, polyoxypropylene myristic acid isopropanolamide, polyoxypropylene stearic acid isopropanolamide, polyoxypropylene palm oil fatty acid isopropanolamide and polyoxypropylene palm kernel oil fatty acid isopropanolamide.

8. The detergent composition according to claim 1, wherein a formulation amount of (C) the polyoxypropylene fatty acid isopropanolamide is 0.5 to 15.0% by weight based on the total weight of the composition.

9. The detergent composition according to claim 1, wherein a formulation amount of (C) the polyoxypropylene fatty acid isopropanolamide is 10 to 5.0% by weight based on the total weight of the composition.

10. The detergent composition according to claim 1, wherein (D) the cationic polymer is at least one selected from the group consisting of a cationic cellulose derivative, cationic starch, cationic guar gum derivative, diallyl quaternary ammonium salt polymerized product, diallyl quaternary ammonium salt/acrylamide copolymerized product and quaternary polyvinylpyrrolidone derivative.

11. The detergent composition according to claim 1, wherein a formulation amount of (D) the cationic polymer is 0.1 to 3.0% by weight based on the total weight of the composition.

12. The detergent composition according to claim 1, wherein a formulation amount of (D) the cationic polymer is 0.3 to 1.5% by weight based on the total weight of the composition.

13. The detergent composition according to claim 1, wherein (E) the water-soluble inorganic salt is at least one salt formed by a monovalent cation selected from a sodium ion, a potassium ion and an ammonium ion and/or a divalent cation selected from a magnesium ion and a calcium ion, with an anion selected from a chlorine ion, a sulfate ion, a phosphate ion, a carbonate ion and a nitrate ion.

14. The detergent composition according to claim 13, wherein (E) the water-soluble inorganic salt is at least one selected from the group consisting of sodium chloride, sodium carbonate, sodium sulfate, sodium hydrogen sulfate, sodium phosphate, sodium hydrogen phosphate, potassium chloride, potassium sulfate, potassium hydrogen sulfate, is potassium phosphate, potassium hydrogen phosphate, potassium dihydrogen phosphate, magnesium chloride, calcium chloride, ammonium sulfate, ammonium phosphate and magnesium sulfate.

15. The detergent composition according to claim 14, wherein (E) the water-soluble inorganic salt is at least one selected from the group consisting of sodium chloride, magnesium chloride, calcium chloride and magnesium sulfate.

16. The detergent composition according to claim 1, wherein a formulation amount of (E) the water-soluble inorganic salt is 0.1 to 3.0% by weight based on the total weight of the composition.

17. The detergent composition according to claim 1, wherein a formulation amount of (E) the water-soluble inorganic salt is 0.3 to 1.5% by weight based on the total weight of the composition.

18. The detergent composition according to claim 1, wherein (F) the amphoteric surfactant is at least one selected from the group consisting of lauryl betaine, lauroylamide propyl betaine and 2-alkyl-N-carboxymethyl-N-hydroxyethyl imidazolinium betaine.

19. The detergent composition according to claim 1, wherein a formulation amount of (F) the amphoteric surfactant is 1.0 to 10.0% by weight based on the total weight of the composition.

20. The detergent composition according to claim 1, wherein a formulation amount of (F) the amphoteric surfactant is 3.0 to 8.0% by weight based on the total weight of the composition.

* * * * *

UNITED STATES PATENT AND TRADEMARK OFFICE
CERTIFICATE OF CORRECTION

PATENT NO. : 7,582,599 B1  
APPLICATION NO. : 12/256805  
DATED : September 1, 2009  
INVENTOR(S) : Matsue It is certified that error appears in the above-identified patent and that said Letters Patent is hereby corrected as shown below:

Column 8, Line 37, Claim 9, "10 to 5.0%" should read -- 1.0 to 5.0% --

Column 8, Line 66, Claim 14, after "hydrogen sulfate", remove the word "is"

Signed and Sealed this

Twelfth Day of January, 2010

David J. Kappos  
*Director of the United States Patent and Trademark Office*